United States Patent
Constandt

(10) Patent No.: US 10,216,696 B2
(45) Date of Patent: Feb. 26, 2019

(54) DATA PROCESSING SYSTEM FOR ADAPTIVE VISUALIZATION OF FACETED SEARCH RESULTS

(71) Applicant: ONTOFORCE NV, Ghent (BE)

(72) Inventor: Hans Constandt, Dilbeek (BE)

(73) Assignee: ONTOFORCE NV, Ghent (BE)

( * ) Notice: Subject to any disclaimer, the term of this patent is extended or adjusted under 35 U.S.C. 154(b) by 373 days.

(21) Appl. No.: 14/913,032

(22) PCT Filed: Aug. 13, 2014

(86) PCT No.: PCT/EP2014/067372
§ 371 (c)(1),
(2) Date: Feb. 19, 2016

(87) PCT Pub. No.: WO2015/024842
PCT Pub. Date: Feb. 26, 2015

(65) Prior Publication Data
US 2016/0210337 A1    Jul. 21, 2016

(30) Foreign Application Priority Data

Aug. 21, 2013 (EP) .................................... 13181131

(51) Int. Cl.
| | | |
|---|---|---|
| G06F 16/00 | (2019.01) | |
| G06F 16/248 | (2019.01) | |
| G06F 16/242 | (2019.01) | |
| G06F 16/2457 | (2019.01) | |
| G06Q 10/10 | (2012.01) | |
| G06F 19/10 | (2011.01) | |
| G06F 19/26 | (2011.01) | |
| G06F 19/28 | (2011.01) | |

(52) U.S. Cl.
CPC ........ *G06F 16/248* (2019.01); *G06F 16/2423* (2019.01); *G06F 16/24575* (2019.01); *G06F 19/10* (2013.01); *G06Q 10/10* (2013.01); *G06F 19/26* (2013.01); *G06F 19/28* (2013.01)

(58) Field of Classification Search
CPC ............. G06Q 10/10; G06F 17/30554; G06F 17/30392; G06F 17/30528; G06F 19/10; G06F 19/26; G06F 19/28
USPC ....................................................... 707/722
See application file for complete search history.

(56) References Cited

U.S. PATENT DOCUMENTS

| | | | | |
|---|---|---|---|---|
| 2003/0097357 A1* | 5/2003 | Ferrari | ............. | G06F 17/30864 |
| 2007/0162443 A1* | 7/2007 | Liu | .................. | G06F 17/30864 |
| 2007/0179952 A1 | 8/2007 | Vespe et al. | | |
| 2007/0283259 A1 | 12/2007 | Barry et al. | | |
| 2009/0198675 A1* | 8/2009 | Mihalik | ............ | G06F 17/30864 |

(Continued)

OTHER PUBLICATIONS

Cleveland et al., "MASFA: Mass-collaborative Faceted Search for Online Communities," World Wide Web Companion, International World Wide Web Conferences Steering Committee, Republic and Canton of Geneva Switzerland, May 13, 2013, pp. 293-296.

(Continued)

*Primary Examiner* — Evan Aspinwall
(74) *Attorney, Agent, or Firm* — Workman Nydegger

(57) ABSTRACT

A system for adaptive visualization of faceted search results comprises a visualization module configured to adapt a predetermined visualization correlation between the data types of the search result facets and the visualization types in function of the aggregated visualization type modifications.

13 Claims, 12 Drawing Sheets

(56) References Cited

U.S. PATENT DOCUMENTS

| | | | |
|---|---|---|---|
| 2009/0249290 A1* | 10/2009 | Jenkins | G06F 17/30011 717/109 |
| 2009/0322756 A1* | 12/2009 | Robertson | G06F 17/30716 345/440 |
| 2009/0322782 A1* | 12/2009 | Kimchi | G06F 17/30554 345/619 |
| 2011/0055246 A1* | 3/2011 | Le Biannic | G06F 17/30392 707/769 |
| 2011/0246458 A1 | 10/2011 | Tuchman et al. | |
| 2012/0023101 A1* | 1/2012 | Heimendinger | G06F 17/30522 707/737 |
| 2013/0097544 A1* | 4/2013 | Parker | G09B 29/003 715/771 |
| 2013/0194294 A1* | 8/2013 | Zhao | G06F 17/30389 345/619 |
| 2014/0047312 A1* | 2/2014 | Ruble | G06T 15/10 715/212 |
| 2014/0047328 A1* | 2/2014 | Ruble | G06T 15/10 715/256 |
| 2014/0129493 A1* | 5/2014 | Leopold | G06F 17/30554 706/12 |

OTHER PUBLICATIONS

Extended European Search Report for corresponding European Application No. 13181131.7, dated Dec. 20, 2013.
International Search Report for corresponding International PCT Application No. PCT/EP2014/067372, dated Oct. 2, 2014.

\* cited by examiner

DATA PROCESSING SYSTEM FOR ADAPTIVE VISUALIZATION OF FACETED SEARCH RESULTS

FIELD OF THE INVENTION

The present invention generally relates to a data processing system for visualisation of search results. This invention more specifically relates to visualisation of faceted search results.

BACKGROUND OF THE INVENTION

Faceted search, also called faceted navigation or faceted browsing, is a technique for accessing information organized according to a faceted classification system. In a context of a search systems accessing a vast amount of information, producing a large number of search results such a faceted classification system allows users to explore and refine the search results by applying suitable filters. Such a faceted classification system enables the possibility to classify search results dynamically, rather than in a single, predetermined, taxonomic order. Facets correspond to properties of the search results. These facets can for example be determined in function of pre-existing fields in a database, that form properties of the search results. Such facets could be determined in function of database fields, such as for example be author, description, language, dates, prices, technical features, etc. This allows for example to refine search results resulting from a query "digital camera" on a database storing items sold through an online shop to be refined by using the following facets, "price", "resolution", "brand", etc. Alternatively or additionally facets could also be determined in function of analysis of the text content related to a search result for example by using entity extraction techniques. Faceted search in this way enables users to navigate a multi-dimensional information space by combining text search with a progressive adaptation of choices in each dimension by means of these facets.

A system for visualisation of search result facets is for example known from US2007179952. Time based facets, which are search result properties that can qualify as dates, time periods, etc. are represented in a linear fashion, for example by means of a time line. Location based facets, which are search result properties that can qualify as countries, gps coordinates, addresses, etc. are for example represented on a map.

Further systems allowing for visualisation of search result facets are generally known from online shops, in which a range of values for a "price" facet is represented as a slider bar by which a minimum and/or maximum value can be set by the user for allowing further filtering of the search results.

Such systems allow for an efficient representation of the facets, especially in a situation where the range of possible values of the facets is large and/or where a textual representation, for example in the form of lists as known from US20070283259, does not clearly show the possible relationship between different values or ranges of values of the facets. These known systems function well within the context of for example an online shop as the properties of the search results qualifying as facets are well known and a suitable visualisation can be linked to them. The same holds for relatively simple facets such as time based facets or location based facets as known from US2007179952.

However, in the context of a search system covering a plurality of large scale databases, in which new databases are added and removed over time and each of these large scale databases themselves evolving over time, such prior art systems present several difficulties. Such search systems are for example in use in the context of pharmaceutical companies in which researchers make use of information contained in large number of databases, for example freely accessible external databases, external databases provided by commercial providers, in-company databases, etc. providing data about for example genes, proteins, clinical data, patient histories, clinical trials, molecules, etc. Every time a new database is made accessible or every time the setup of an existing database is changed, the search system, extensive programming and configuration is necessary in order to determine the correct way of visualisation for the relevant facets of the search results. Furthermore determination of the preferred way of visualisation of such complex data is not an easy task for a programmer to perform and often requires extensive consultation of end users and/or results in a sub-optimal user experience.

There still exists a need to improve flexibility and efficiency of the visualisation of faceted search results in the context of such a large scale, complex faceted search system.

SUMMARY OF THE INVENTION

According to a first aspect of the invention there is provided a data processing system for adaptive visualisation of faceted search results comprising:
  an input module configured to receive a search query;
  a retrieval module connected to said input module and configured to:
    receive from said input module said search query; and
    retrieve a plurality of search results in function of said search query, each of said search results comprising a plurality of search result properties of which at least one of the search result properties is a search result facet;
  a data type determination module connected to said retrieval module and configured to:
    receive one or more of said search result facets from said retrieval module; and
    determine the data type of one or more of said search result facets
  a visualisation type association module connected to said data type determination module and configured to:
    receive said data type from said data type determination module; and
    associate a visualisation type with said data type in function of a predetermined visualisation correlation between said data type and said visualisation type;
  a visualisation module connected to said visualisation type association module and said retrieval module and configured to:
    receive said one or more search result facets from said retrieval module and said visualisation types from said visualisation type association module;
    present said one or more search result facets by means of a visualisation in function of said visualisation types to one or more users; and
    present visualisation modifiers to said one or more users configured to request a visualisation type modification by said one or more users of the visualisation type of said presented visualisation;
  a modification aggregator connected to said visualisation module and configured to:
    receive said visualisation type modifications from said visualisation module; and
    aggregate said visualisation type modifications;

a correlation adaptation module connected to said modification aggregator and said visualisation type association module, and being configured to:
  exchange said aggregated visualisation type modifications with said modification aggregator and said predetermined visualisation correlation with said visualisation type association module; and
  adapt said predetermined visualisation correlation between said data types of said search result facets and said visualisation types in function of said aggregated visualisation type modifications.

In this way, even when the initial predetermined visualisation correlation 44 that is set up, for example when a new database is added to the faceted search system 1 is suboptimal, based on user feedback the system will automatically adapt during use in order to attain a more optimized setup. This greatly reduces overhead and flexibility when coping with the introduction of new data sources or changes to existing data sources.

According to an embodiment:
  said retrieval module is further configured to retrieve a plurality of search results of which at least one of the search result properties is a non-facet search result property that is not a search result facet;
  said data type determination module is further configured to determine the data type of said non-facet search result properties.
  said visualisation module is further configured to:
  receive said one or more non-facet search result properties from said retrieval module and said visualisation types from said visualisation type association module;
  present said one or more non-facet search result properties by means of a visualisation in function of said visualisation types to one or more users; and
  present visualisation modifiers to said one or more users configured to request a visualisation type modification by said one or more users of the visualisation type of said presented visualisations.

Although this adaptive visualisation is especially useful for intuitively structuring search result facets of large scale information sources for enabling further filtering or navigation, it is clear that according to this further optional embodiment, this adaptive visualisation behaviour could additionally be useful when applied to non-facet search result properties.

According to a further embodiment the correlation adaptation module is further configured adapt said predetermined visualisation correlation when said aggregated visualisation type modifications exceed a predetermined threshold.

This is especially useful in a multi-user context in order to allow for additional flexibility while limiting the effect of occasional or random changes to the visualisation type by users.

According to a preferred embodiment:
  a modification aggregator is further configured to aggregate visualisation type non-modifications of said presented visualisation types by said one or more users; and
  the correlation adaptation module is further configured to determine said predetermined threshold as a predetermined rate of said aggregated visualisation type modifications versus said aggregated visualisation type non-modifications.

This is especially useful in a multi-user context and allows for a further refinement of control of allowed flexibility versus robustness against the effect of occasional or random changes to the visualisation type by users.

Optionally said visualisation types comprise one or more of the following:

a bar chart;
a pie chart;
a one dimensional range;
a two dimensional heat map;
a hierarchical, multi-dimensional tree;
a Molecule Viewer;
a Pathway View;
a Protein Interaction View;
a Sequence Alignment View.

According to a further preferred embodiment:
a visualisation module is further configured to:
present a visualisation in function of said visualisation types to one or more users comprising a range selector configured to request a range selection of a range of values associated with said search result facets;
exchange said range selection with said retrieval module;
Said retrieval module further configured to:
adapt said search query by means of said range selection; and
retrieve a plurality of search results in function of said adapted search query.

This allows for an efficient and user friendly setup that allows for interactive faceted filtering an navigation.

According to a second aspect of the invention there is provided a computer implemented method for adaptive visualisation of faceted search results comprising the steps of:
  receiving a search query;
  retrieving a plurality of search results in function of said search query, each of said search results comprising a plurality of search result properties of which at least one of the search result properties is a search result facet;
  determining the data type of one or more of said search result facets;
  associating a visualisation type with said data type in function of a predetermined visualisation correlation between said data type and said visualisation type;
  presenting said one or more search result facets by means of a visualisation in function of said visualisation types to one or more users
  presenting visualisation modifiers to said one or more users configured to request a visualisation type modification by said one or more users of the visualisation type of said presented visualisation;
  aggregating said visualisation type modifications;
  adapting said predetermined visualisation correlation between said data types of said search result facets and said visualisation types in function of said aggregated visualisation type modifications.

According to a third aspect of the invention there is provided a computer readable medium comprising computer-executable instructions, which when executed by a data processing system, perform the method according to the second aspect of the invention.

DETAILED DESCRIPTION OF EMBODIMENT(S)

Figure 1:
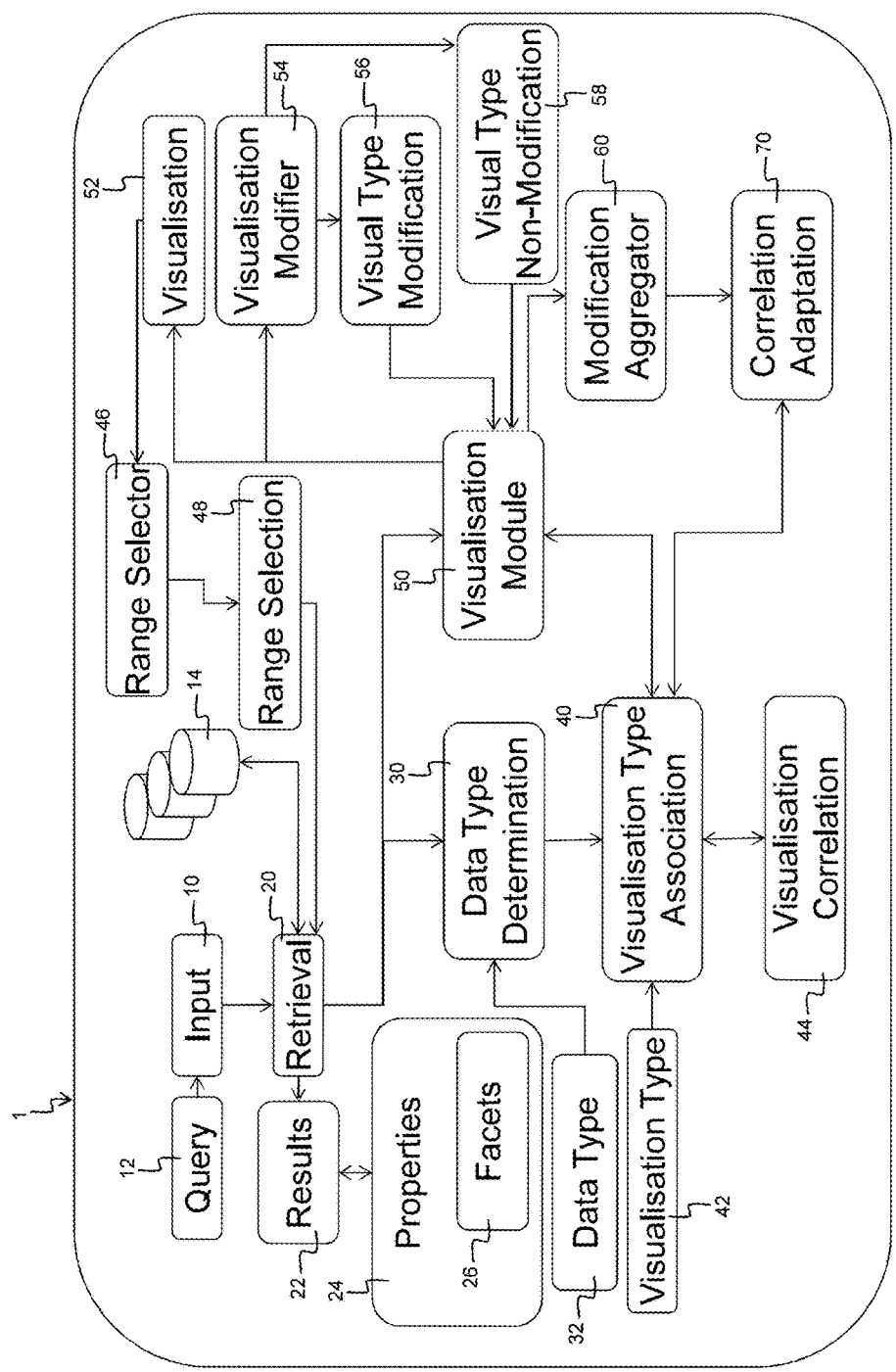
FIG. 1 schematically illustrates a data processing system for adaptive visualisation of faceted search results.

An embodiment of a data processing system 1 for adaptive visualisation of faceted search results also referred to as faceted search system. It comprises an input module 10 by which the system can receive a search query 12 from a user. Such an input module 10 could for example receive a search query 12 from a suitable input box on a user interface, such as for example shown in FIG. 2. As further shown in FIG. 1 a retrieval module 20, that is connected to the input module 10, receives this search query 12 from the input module 10. As shown the retrieval module 20 will subsequently retrieve a plurality of search results 22 in function of this search query 12. These search results 22 could for example be suitable results from a query based on the search query 12 performed on one or more databases 14. The search query 12 could for example relate to a specific disease "Artherosclerosis" and a type of publications "Assay". The retrieval module will translate these keywords to suitable instructions for retrieval of search results in an freely available external database, a commercial external database, an in-company database, etc. The search results 22 returned by these databases will be organized by the retrieval module 20 such that, each of these search results 22 has a plurality of search result properties 24, preferably in such a way that the search result properties 24 for search results 22 of the different databases are harmonized so that for example a single search result property 24 becomes available for the publication date of each search result 22 irrespective of the originating database. At least one of the search result properties 24 should qualify as a search result facet 26, this means that it should allow for a range of values that allow for further filtering or faceted navigation. Examples of properties that could qualify as a search result facet 26 are for example publication dates, dates of phases of clinical trials, phases of clinical trials, publication types, names of authors, names of pharmaceutical companies, target diseases, type of test subject, therapeutic area, etc. Each of these facets allow for further filtering, for example by limiting the range of publication dates or to provide pointers to additional search results, for example by providing links to other search results for the top 5 authors, top 10 related target diseases related to search results 22 of the current query. It is clear that search result properties 24 such as for example unique identifiers, title, abstract, etc. as such would not qualify as a search result facet 26.

A data type determination module 30 connected to the retrieval module 30 then receives these search result facets 26 from the retrieval module 20 so that it can determine their data type 32. Search result facets 26 such as publication date or other time based search result facets 26 can receive a "data/time" tag as data type 32. Search result facets 26 such as authors, inventor, speaker can receive a "person" tag as data type. Other suitable data types 32 could be available for search result properties 24 related to gene sequences, molecules, diseases, companies, geographic information, target disease, etc. A visualisation type association module 40 is connected to this data type determination module 30 in order to link a suitable visualisation type 42 to each of these data types 32. The visualisation type association module 40 is provided with the data type 32 from the data type determination module 30 and associates a visualisation type 42 with this data type 32. This association of the visualisation type 42 is performed in function of a predetermined visualisation correlation 44 between the data type 32 and the visualisation type 42. Such a predetermined visualisation correlation 44 could for example be implemented by means of a suitable concordance table between the data type 32 and the visualisation type 42. Examples of such visualisation types 42 are for example a bar chart, a pie chart, a one dimensional range, a two dimensional heat map, a hierarchical, multi-dimensional tree, a Molecule Viewer, a Pathway View, a Protein Interaction View, a Sequence Alignment View, etc. The predetermined visual correlation 44 could for example determine that the data type 32 of a search result facet 26 related to a publication date is linked to a one dimensional range visualisation type 42 allowing further filtering of the search results. According to another example the predetermined visual correlation 44 could for example determine that the data type 32 of a search result facet 26 related to a target disease is best represented as a two dimensional heat map of which the size or colour of the individual parts is related to the number of search results 22 comprising this particular value of the search result facet 26. It is clear that numerous alternative examples of the predetermined visual correlation 44 are possible.

Subsequently the search result facets 26 and their related visualisation type 42 is provided to the visualisation module 50 by the visualisation type association module 40 and the retrieval module 20 respectively. Based on this information the visualisation module 50 presents the search result facets 26 to the users by means of a visualisation 52 in function of the visualisation types 42. This is for example shown in FIG. 2, in which two search result facets 26, one for "drugs" and one for "target diseases". Both these facets have data types 32 that are correlated to a heat map visualisation type 42 by the visualisation type association module 40. Additionally the visualisation module 50 presents visualisation modifiers 54 to the users configured. By means of these visualisation modifiers 54, also shown in FIG. 2, the users are able to request a visualisation type modification 56. This means that these visualisation modifiers 54 allow the users to change the visualisation type 42 of the presented visualisation 52. In the example shown in FIG. 2, this could mean that the heat map visualisation type 42 of the "drugs" search result facet 26 is for example changed to a histogram visualisation type 42 by the user by accessing a number of choices offered by means of the visualisation type modifier 54. When the user enters his/her choice this request for a visualisation type modification 56 is sent to a modification aggregator 60 connected to the visualisation module 50. This modification aggregator 60 keeps track of all visualisation type modifications 56 of the users of the faceted search system by aggregating these visualisation type modifications 56. The aggregated visualisation type modifications 56 are exchanged by the modification aggregator 60 with a correlation adaptation module 70. This correlation adaptation module 70 is able to automatically adapt the predetermined visualisation correlation 44 between the data types 32 of the search result facets 26 and the visualisation types 42 in function of these aggregated visualisation type modifications 56. In order to do so it is suitably connected to the visualisation type association module 40, for exchange of the predetermined visualisation correlation 44. This means that, for example, when a user changes the visualisation type 42 of the "drugs" search result facet 26 from a heat map visualisation type 42 to a histogram visualisation type 42, the predetermined visualisation correlation 44 will get updated accordingly. In this way, even when the initial predetermined visualisation correlation 44 that is set up, for example when a new database is added to the faceted search system 1 is sub-optimal, based on user feedback the system will automatically adapt during use in order to attain a more optimized setup. This greatly reduces overhead and flexibility when coping with the introduction of new data sources or changes to existing data sources.

Although this adaptive visualisation is especially useful for intuitively structuring search result facets of large scale information sources for enabling further filtering or navigation, it is clear that according to a further optional embodiment, this adaptive visualisation behaviour could additionally be useful when applied to non-facet search result properties 28 retrieved by the retrieval module. Such non-facet search result properties 24 which do not qualify as a search result facet 26, could however also benefit from a visual representation. The molecule view presented in FIG. 5A, which will be explained in further detail below, can for example present a schematic representation of the molecule of the active element associated with a non-facet search result property 24. The search results 22 of which at least one of the search result properties 24 is a non-facet search result property 28 are also retrieved by the retrieval module 20 and provided to the data type determination module 30 to determine the data type 32 of said non-facet search result properties 28. Similarly as explained above with reference to the search result facets 26 the visualisation module 50 will present these non-facet search result properties 28 by means of a visualisation 52 in function of the visualisation types 42 linked to the data types 32 to the users. Additionally also visualisation modifiers 54 will be presented to the users enabling them to request a visualisation type modification 56 that will be subsequently handled similarly as described above. This According to the embodiment shown in FIG. 1, in order to control the amount of changes to the predetermined visualisation correlation 44, the correlation adaptation module 70 only adapts the predetermined visualisation correlation 44 when the aggregated visualisation type modifications 56 exceed a predetermined threshold 72. This means that as soon as for example more than ten or twenty or any other suitable number of visualisation type modifications 56 from the current visualisation 52 to a specific new visualisation 52 have been aggregated the correlation adaptation module 70 will adapt the predetermined visualisation correlation 44 for this search result facet 26. This is especially useful in a multi-user context in order to allow for additional flexibility while limiting the effect of occasional or random changes to the visualisation type 42 by users. As still a further refinement, as shown in the embodiment of FIG. 1, the modification aggregator 60 also aggregates visualisation type non-modifications 58 of the presented visualisation types 42, which means that it aggregates how many users prefer not to modify the presented visualisation 52. The correlation adaptation module 70 is then able to determine the predetermined threshold 72 as a predetermined rate of the aggregated visualisation type modifications 56 versus the aggregated visualisation type non-modifications 58. The threshold 72 could for example be determined as a rate of 10% or 20% or any other suitable rate of aggregated modifications 56 versus non-modifications 58.

Figure 2:
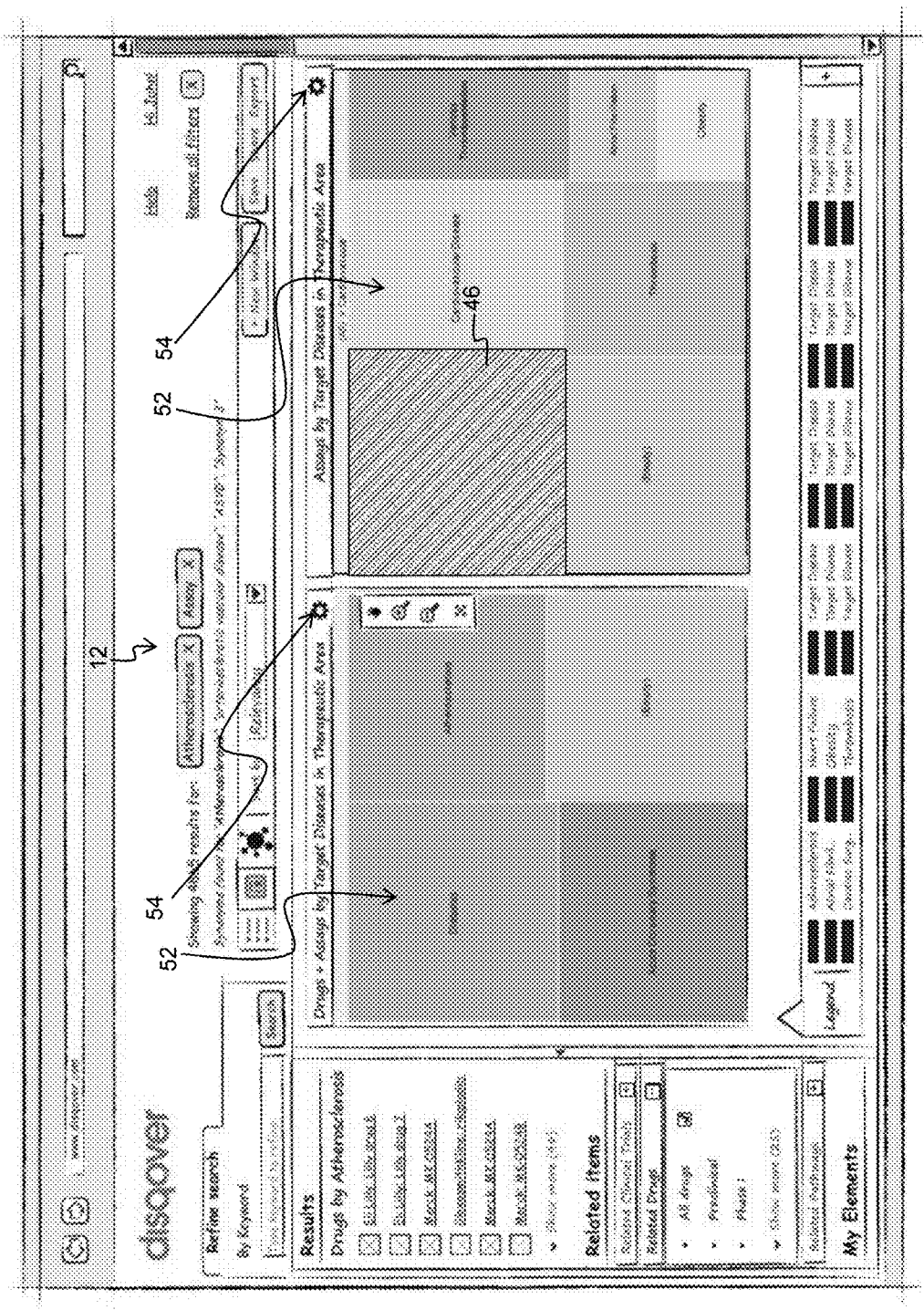
FIG. 2 illustrates an example of a user interface for the data processing system of FIG. 1.

As further shown, according to the embodiment of FIG. 1, the visualisation 52 presented by the visualisation module 50 comprises a range selector 46. As shown in FIG. 2, this range selector 46 for a visualisation type 42 that is a heat map could be implemented as a selectable sector of this heatmap. It is clear that alternative embodiments are possible, such as for example, displaceable sliders in the context of a linear range visualisation type 42, selectable bars in the context of a bar chart visualisation type 42, etc. Such a range selector 46 allows the user to issue a request for a range selection 48 of a range of values associated with the search result facets 26. In the example shown in FIG. 2, one or more specific target diseases are selected in order to further refine the search query or to navigate to related search results by means of these search result facets. The range selection 48 is exchanged with the retrieval module 20, which then adapts the search query 12 by means of the range selection 48. Subsequently the retrieval module 20 retrieve search results 22 in function of this adapted search query 12 and update the user interface accordingly.

Figure 3:
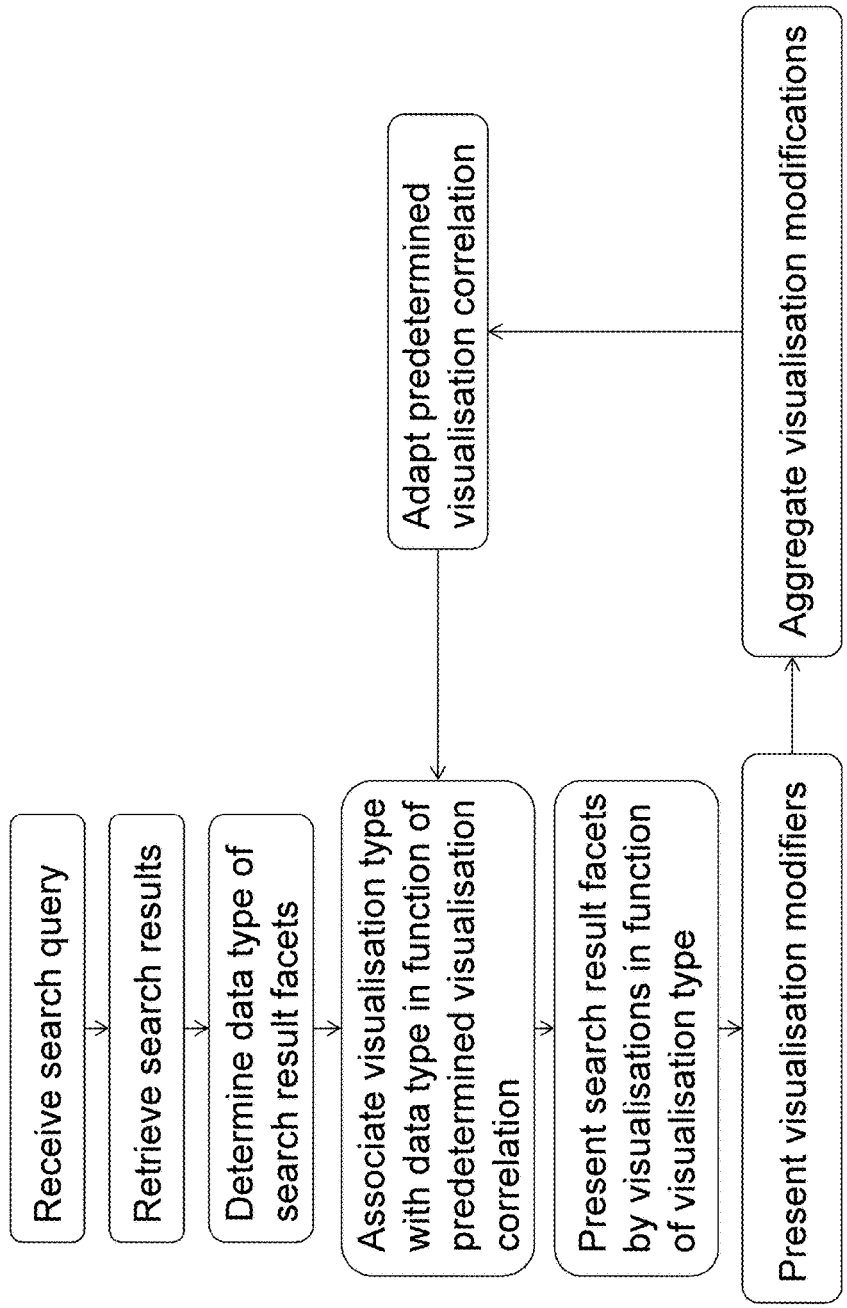
FIG. 3 illustrates a method for operating a data processing system for adaptive visualisation of faceted search results.

Although a specific embodiment of the data processing system 1 has been explained with reference to FIGS. 1 and 2, it is clear that in general the data processing system is operated by means of a computer implemented method for adaptive visualisation of faceted search results performing the steps shown in FIG. 3. Such a computer implemented method could be provided as computer-executable instructions on a computer readable medium, which when executed by a data processing system, perform this method. In a first step the search query 12 is received from the user, subsequently a plurality of search results 22 is retrieved in function of this search query 12. Each of these search results 22 comprises a plurality of search result properties 24 of which at least one of should be a search result facet 26 as explained above. Next the data type 32 of these search result facets 26 is determined. The data type is then associated with a visualisation type 42 in function of a predetermined visualisation correlation 44 between said data type 32 and said visualisation type 42. Then the search result facets 26 are presented to the users by means of a visualisation 52 in function of the visualisation types 42 linked to these search result facets 26 in the previous step. Additionally visualisation modifiers 54 are presented to the users enabling them to request a visualisation type modification 56 in order to modify the visualisation type 42 of the presented visualisation 52. These visualisation type modifications 56 are aggregated and the predetermined visualisation correlation 44 between the data types 32 of the search result facets 26 and said visualisation types 42 is adapted in function of these aggregated visualisation type modifications 56.

Figure 4:
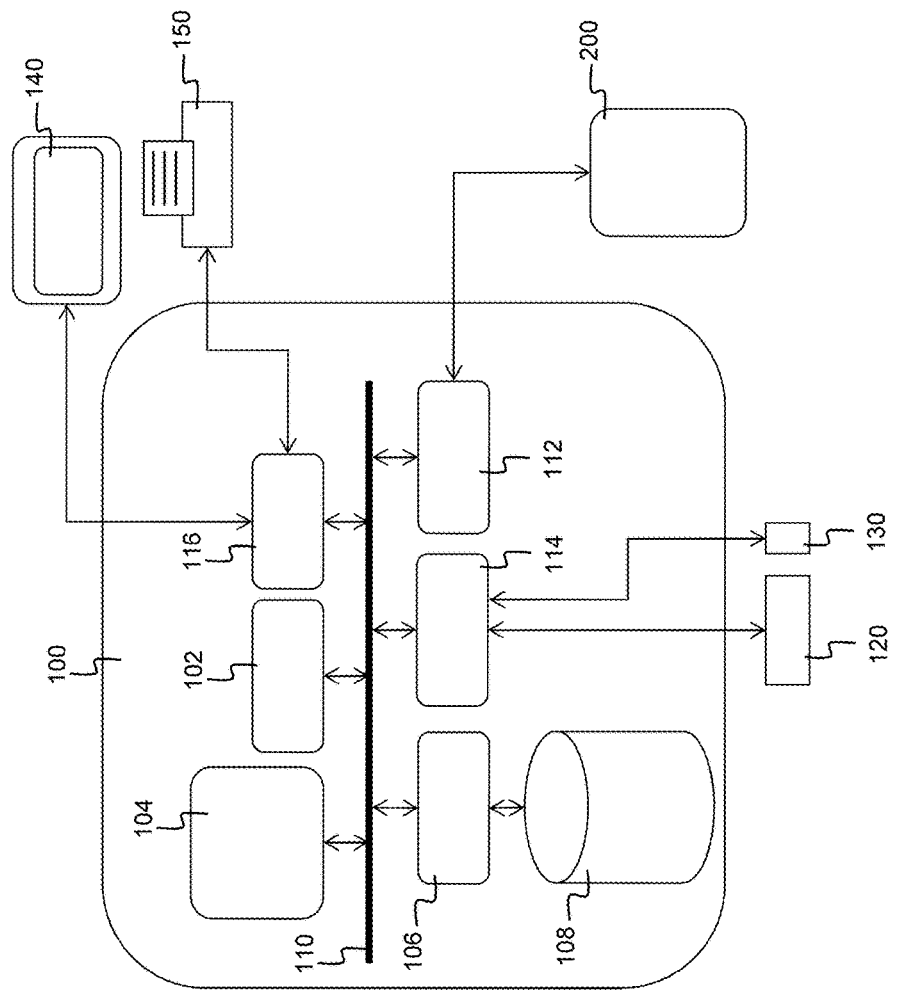
FIG. 4 shows a suitable computing system for hosting the data processing system of FIG. 1.

FIG. 4 shows a suitable computing system 100 for hosting the data processing system of FIG. 1. Computing system 100 may in general be formed as a suitable general purpose computer and comprise a bus 110, a processor 102, a local memory 104, one or more optional input interfaces 114, one or more optional output interfaces 116, a communication interface 112, a storage element interface 106 and one or more storage elements 108. Bus 110 may comprise one or more conductors that permit communication among the components of the computing system. Processor 102 may include any type of conventional processor or microprocessor that interprets and executes programming instructions. Local memory 104 may include a random access memory (RAM) or another type of dynamic storage device that stores information and instructions for execution by processor 102 and/or a read only memory (ROM) or another type of static storage device that stores static information and instructions for use by processor 104. Input interface 114 may comprise one or more conventional mechanisms that permit an operator to input information to the computing device 100, such as a keyboard 120, a mouse 130, a pen, voice recognition and/or biometric mechanisms, etc. Output interface 116 may comprise one or more conventional mechanisms that output information to the operator, such as a display 140, a printer 150, a speaker, etc. Communication interface 112 may comprise any transceiver-like mechanism such as for example two 1 Gb Ethernet interfaces that enables computing system 100 to communicate with other devices and/or systems, for example mechanisms for communicating with one or more other computing systems 200. The communication interface 112 of computing system 100 may be connected to such another computing system by means of a local area network (LAN) or a wide area network (WAN, such as for example the internet, in which case the other computing system 200 may for example comprise a suitable web server. Storage element interface 106 may comprise a storage interface such as for example a Serial Advanced Technology Attachment (SATA) interface or a Small Computer System Interface (SCSI) for connecting bus 110 to one or more storage elements 108, such as one or more local disks, for example 1 TB SATA disk drives, and control the reading and writing of data to and/or from these storage elements 108. Although the storage elements 108 above is described as a local disk, in general any other suitable computer-readable media such as a removable magnetic disk, optical storage media such as a CD or DVD, -ROM disk, solid state drives, flash memory cards, . . . could be used.

The components of the data processing system 1, such as the visualisation module 50, the modification aggregator 60, correlation adaptation module 70, etc. can be implemented as programming instructions stored it local memory 104 of the computing system 100 for execution by its processor 102. Alternatively these components could be stored on the storage element 108 or be accessible from another computing system 200 through the communication interface 112. The same holds for the search results 22, search result properties 24, search result facets 26, etc, which could also be suitably accessible for processing from the local memory 104, the storage element 108 or another computing system 200, for example comprising a suitable database system 14.

Figure 5A:
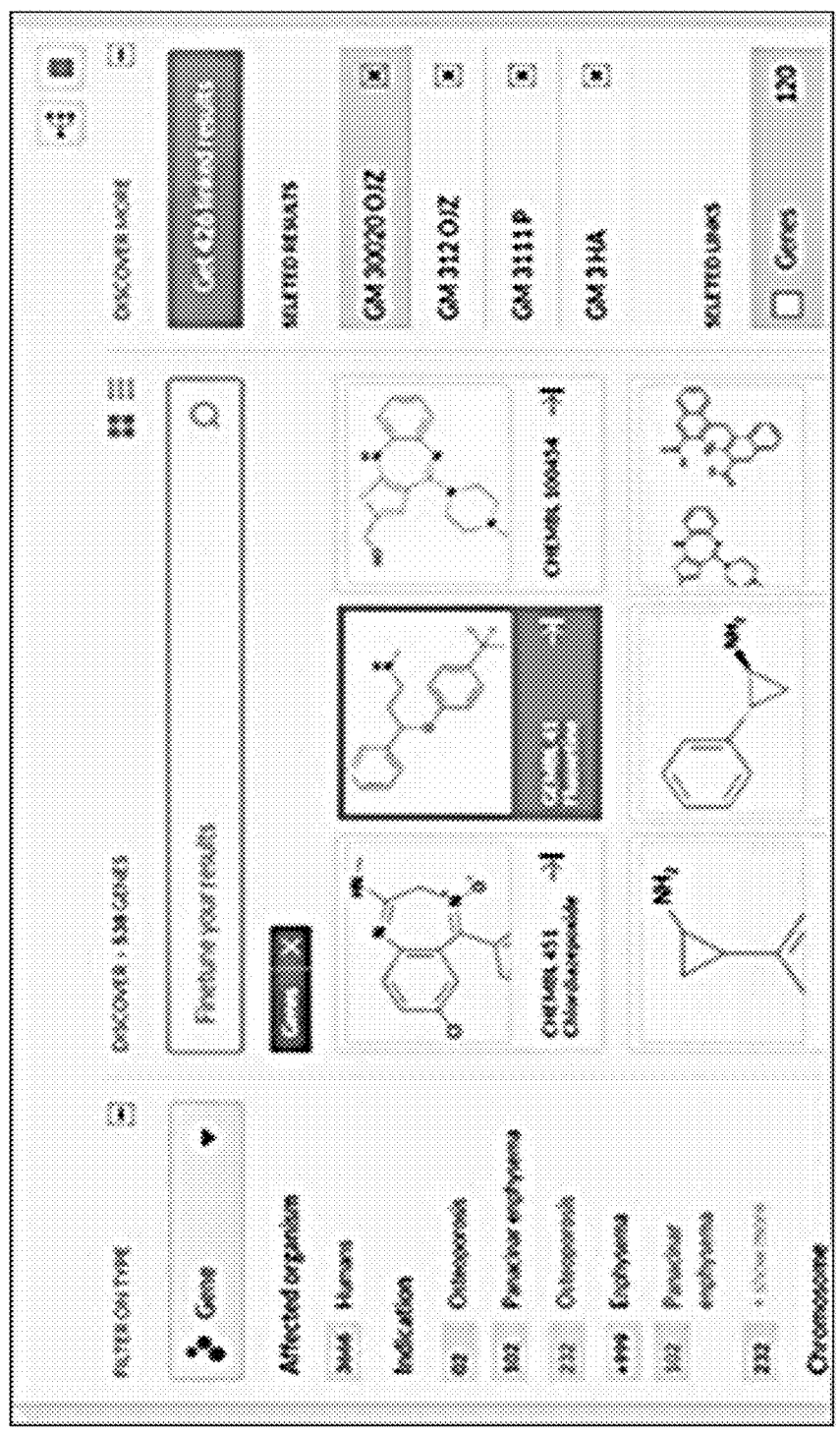
FIGS. 5A-5H show a plurality of further examples of visualisation types.
Figure 5B:
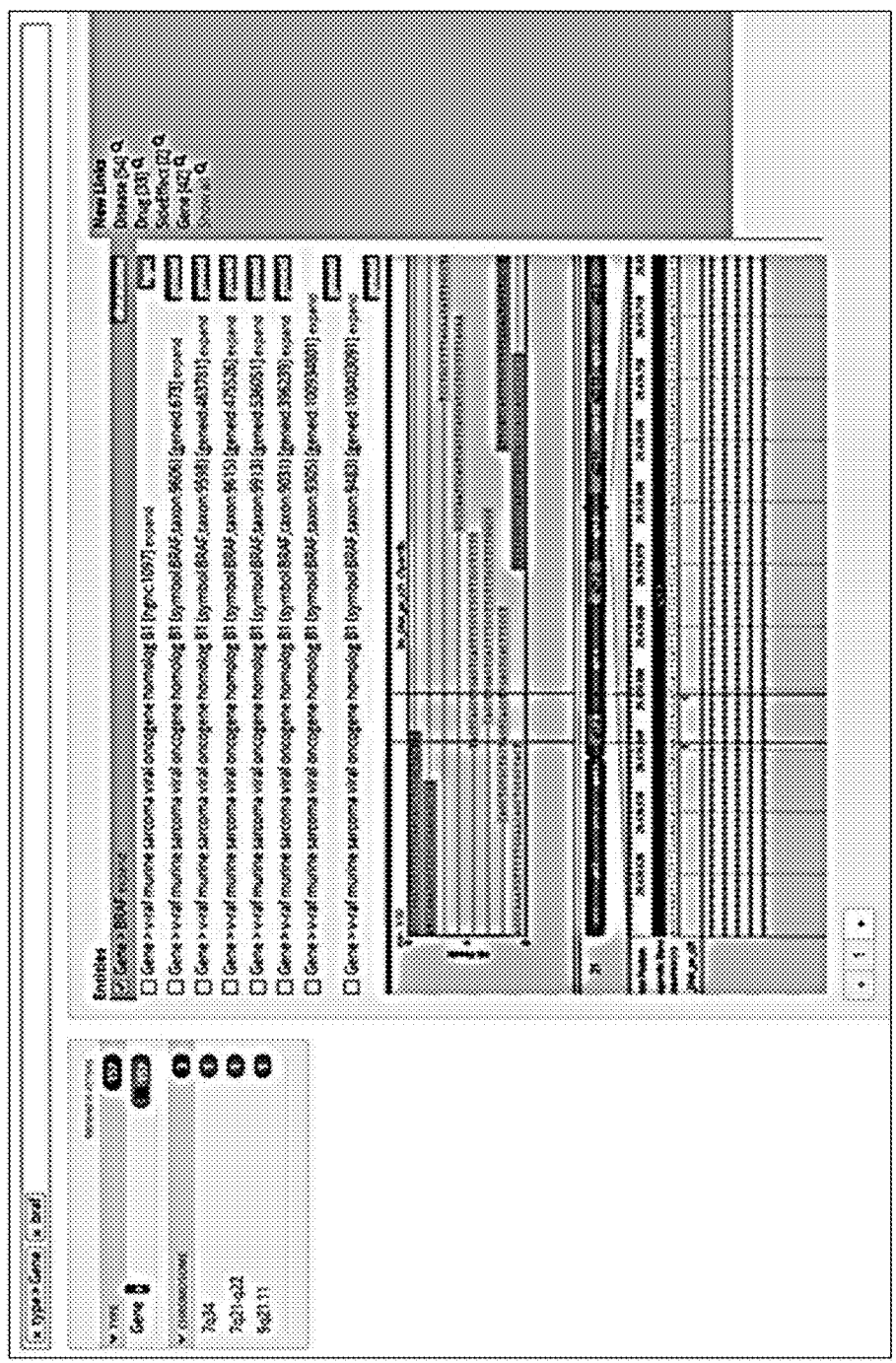
Figure 5C:
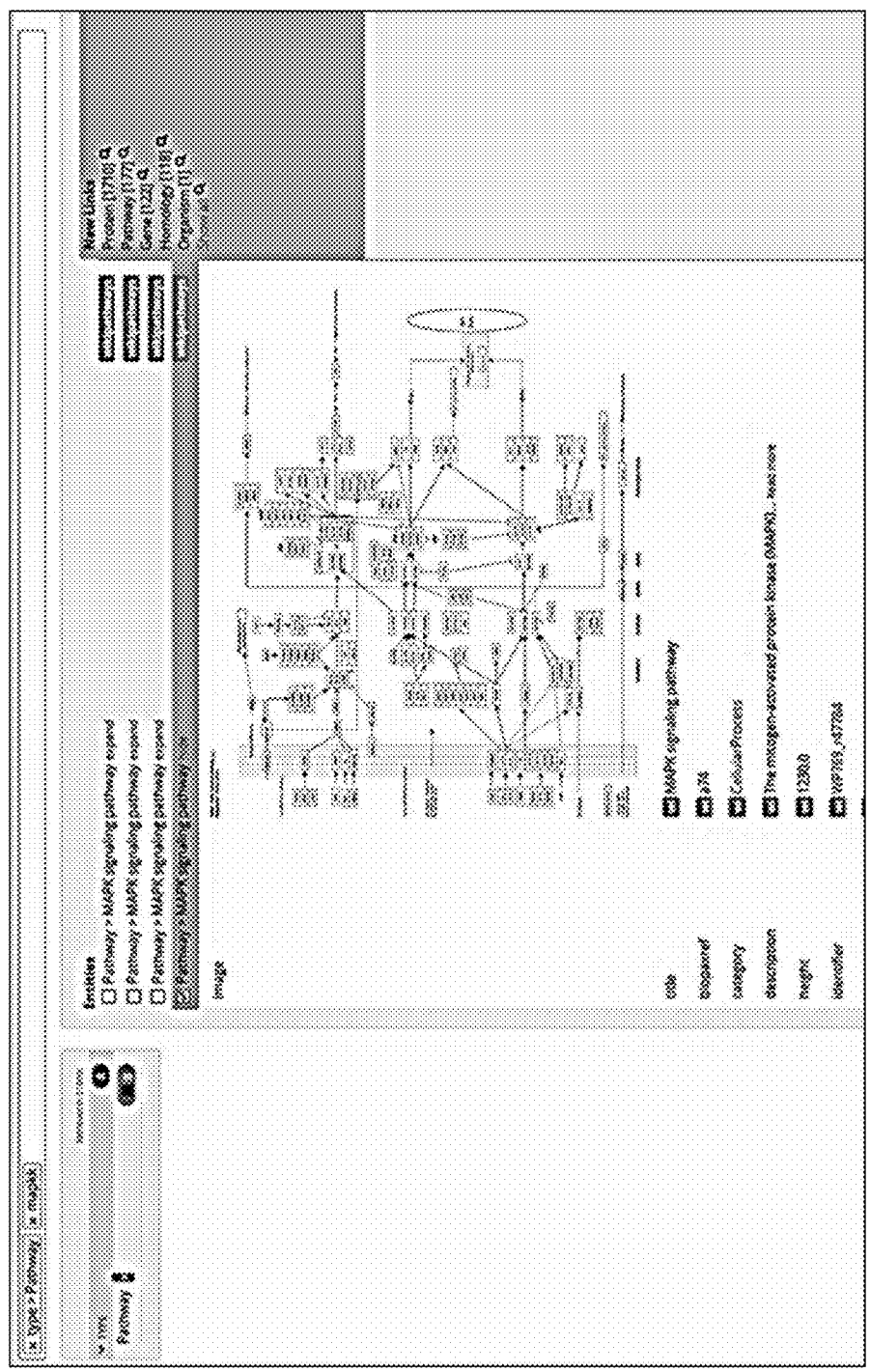
Figure 5D:
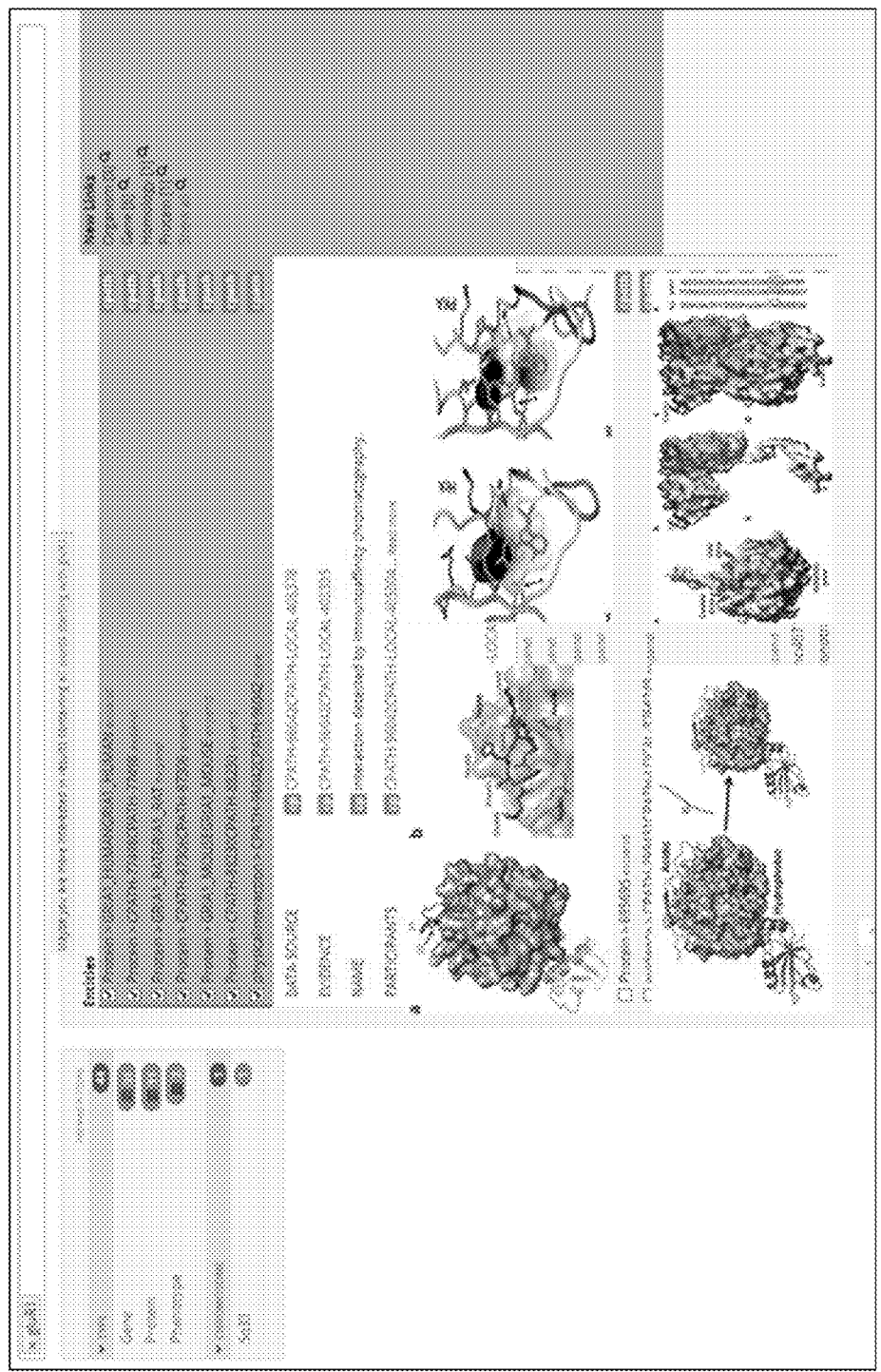
Figure 5E:
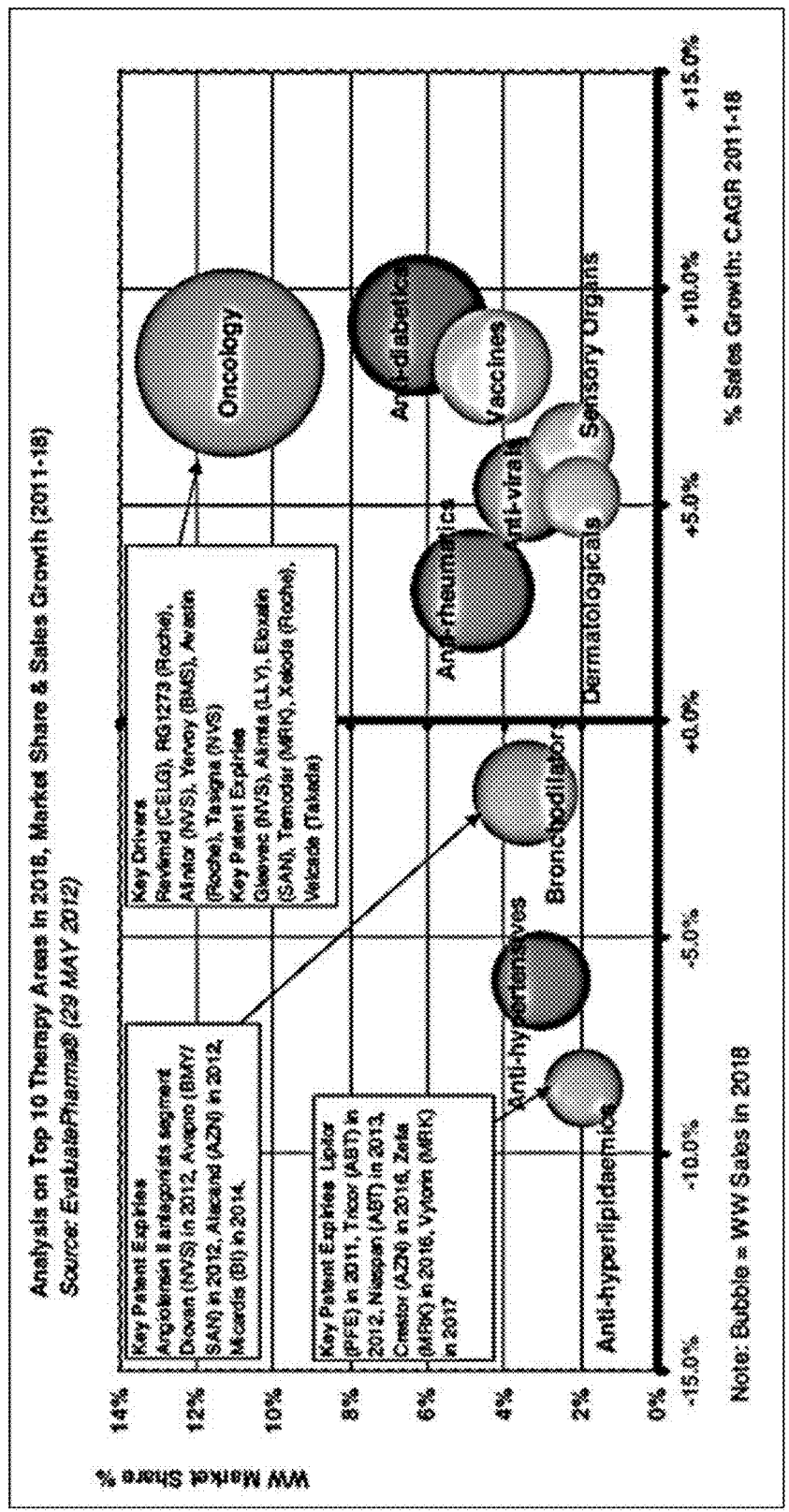
Figure 5F:
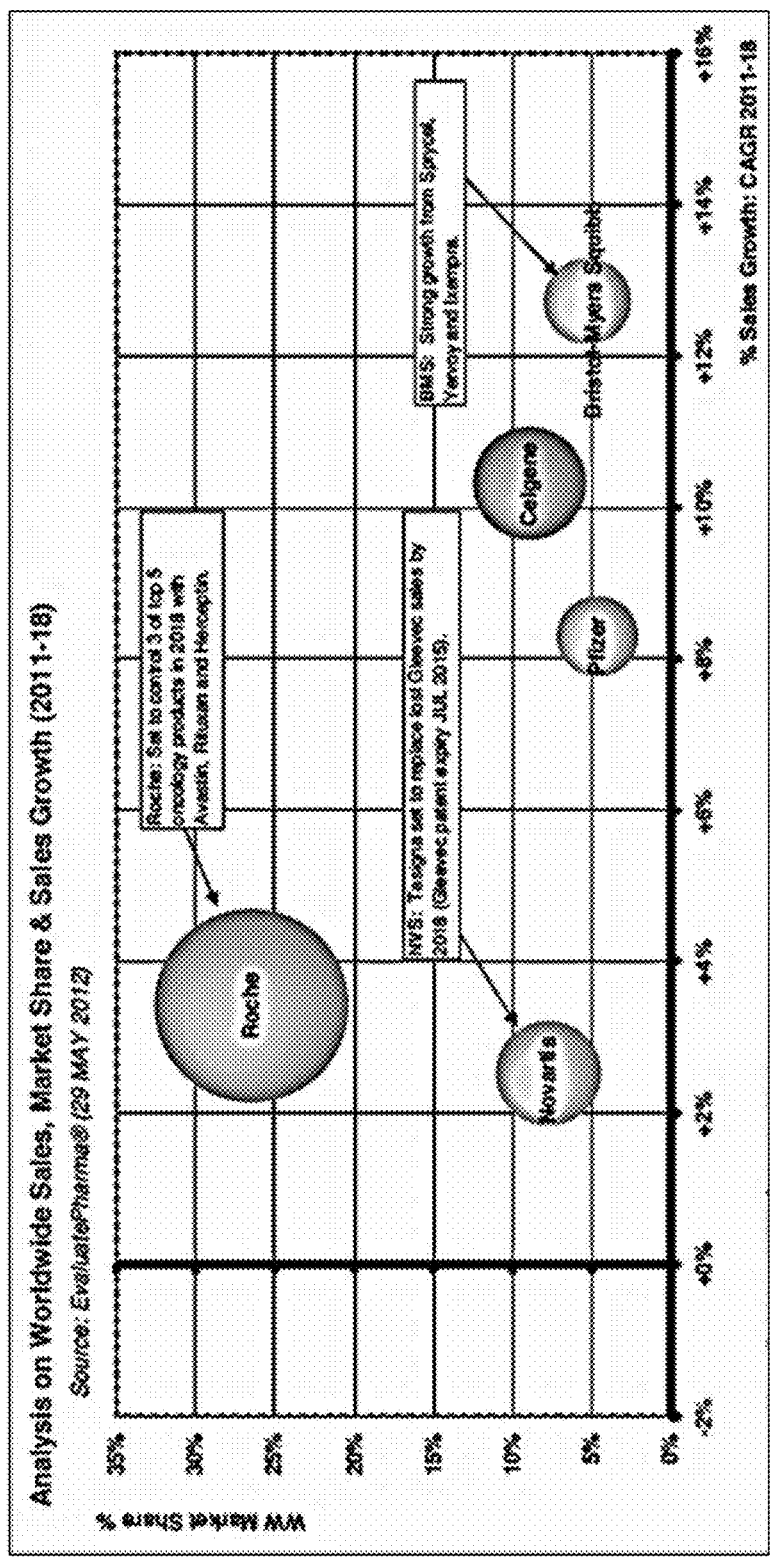
Figure 5G:
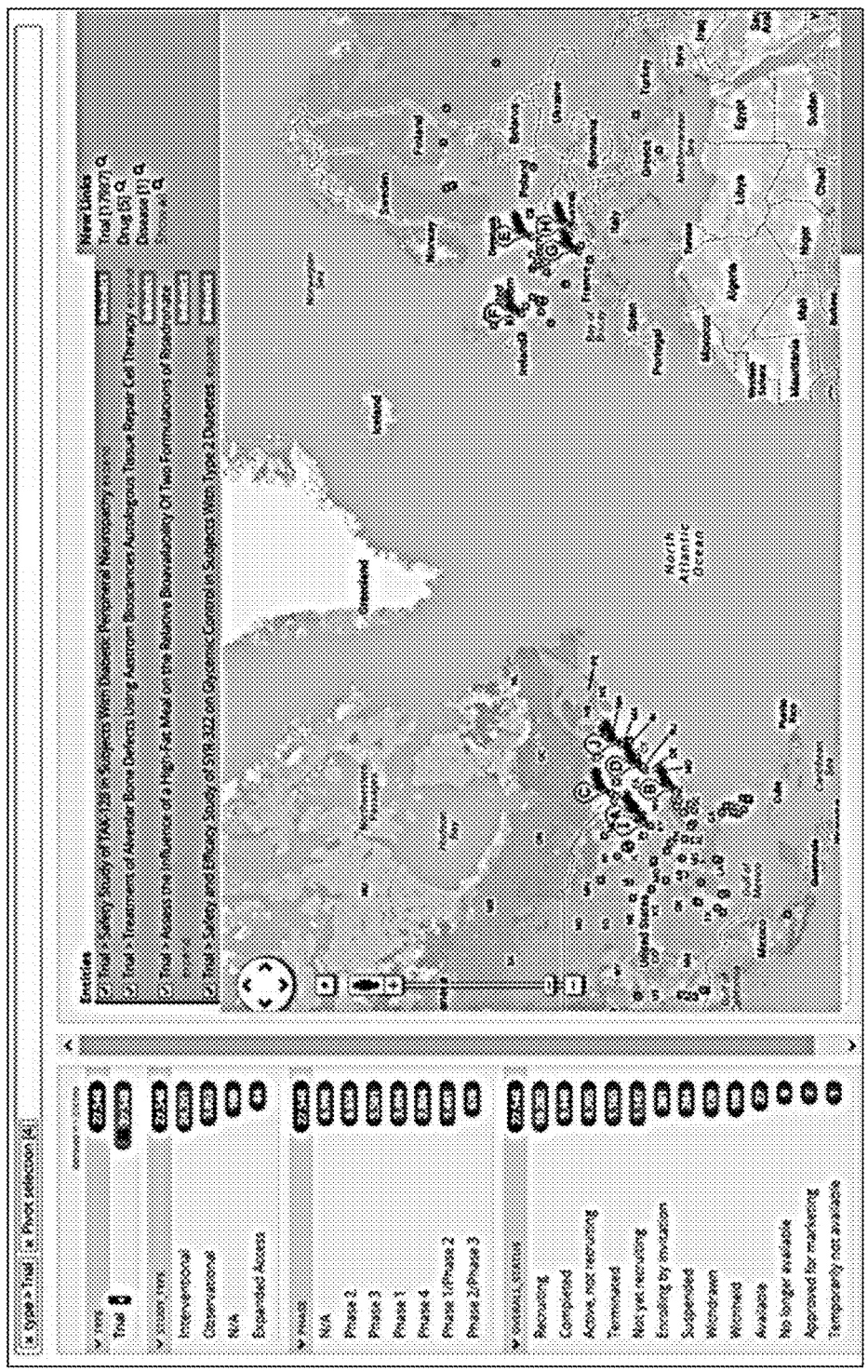
Figure 5H:
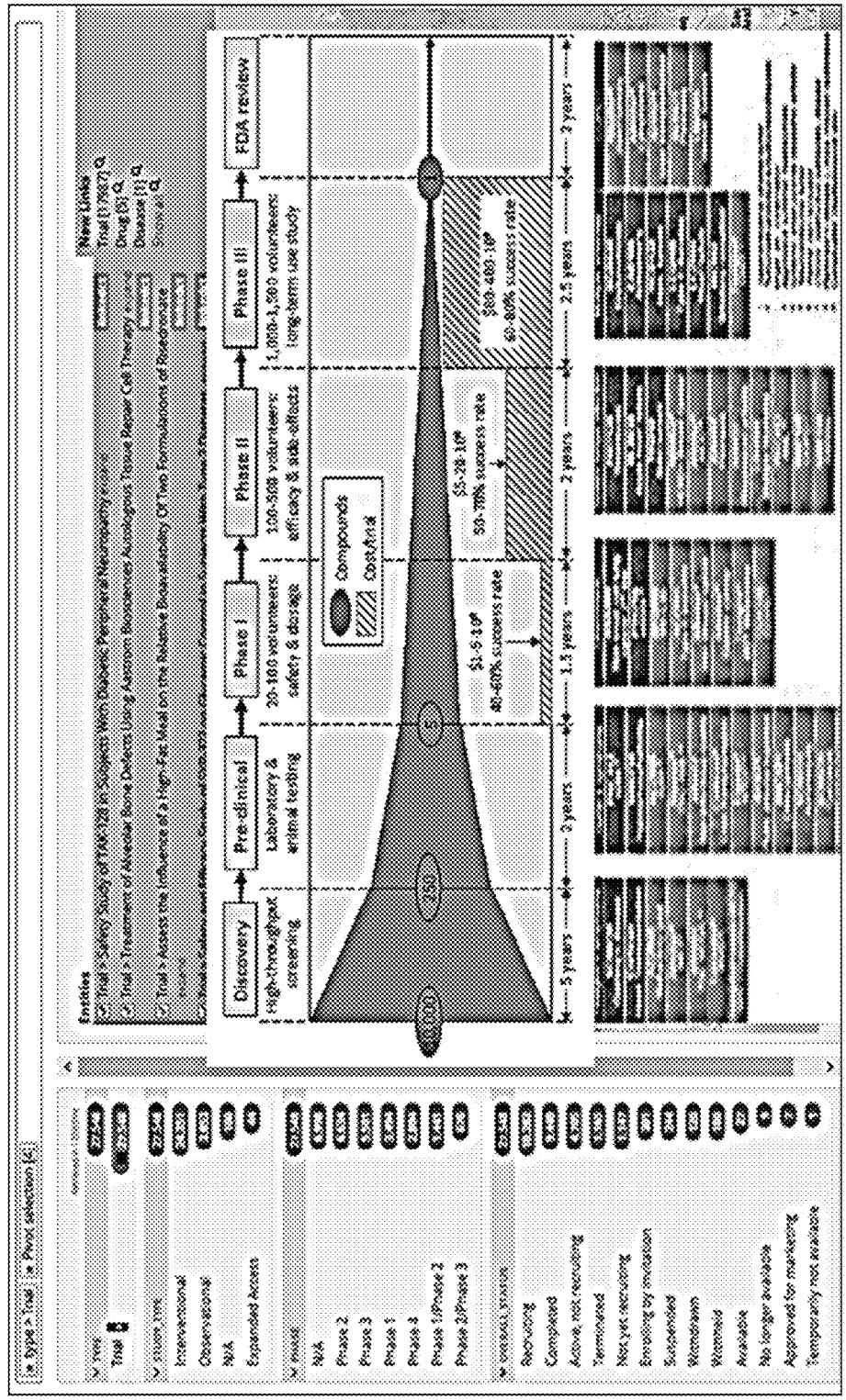

FIGS. 5A-5H show a plurality of further examples of possible visualisation types 42. FIG. 5A shows a molecule viewer, that presents search result properties 24, for example containing chemical formulations for the molecules of an active pharmaceutical ingredient associated with a search result 22. In this way a chemist is presented with a tile view that allows them to analyse which molecules contain specific structures and quickly judge the associated impact, which would not be possible when such search result properties 24 would be presented as a simple empirical formula. This could for example allow for a quick selection of typical benzene structures of interest to the particular research at hand. FIG. 5B shows a sequence alignment view in which gene sequences are aligned an visualised in a way that allows a biologist to make a quicker selection then when presented with a list of gene names. This enables a biologist to easily see what overlap exists in particular chromosomes or organisms, or alternatively quickly find similar genes with a predefined alignment factor. FIG. 5C shows a Pathway View in which researchers are presented in a visual way how the genes are interacting. Pathways are a good way to show where the genes intervene or relate to other critical genes or higher level mechanisms or mode of actions. Typical Pathways also present the researcher with information about the impact as a choice of mode of action in order to influence the action of the genes. Such a Pathway View visualisation type 42 can be analysed more efficiently by a researcher than for example a list of names as these researchers are familiar with the visualisations of the pathways associated with their domain of research, which also allows for an efficient identification of unknown pathways, which can then be easily interpreted from their schema, location and particular mechanisms. FIG. 5D shows a Protein Interaction View in which Chemists are presented visualisations of how proteins associated with a search result property of the search results interact. In this way an efficient way for identifying in which pocket there are binding sites available and where potential drugs or biotechnology mechanisms could interact. Analysing such information in a text format would be very time consuming to analyse. FIGS. 5E and 5F show an example of a 2 dimensional Bubble View of Therapeutic Areas Sales Growth which graphically visualizes search result properties, such as worldwide market share and percentage of sales growth of the search results. Competitive intelligence researchers as well market share analysts in this way are able to quickly analyse growth of markets or to see worldwide oncology sales and its evolution. Bubble charts are a good way to show sales and compound annual growth rate (CAGR). FIG. 5G shows a map view for presenting location data. Such location data could for example be provided by search result properties of search results comprising location data associated with clinical trials. This allows researchers to quickly analyse or select the clinical trials in a specific phase in a specific geographical area. Such visualisations allow to efficiently check availability and proximity to a particular geographic region of interest. FIG. 5H shows a visualisation referred to as a pharma rocket model view. Also the researchers want to see projects or results in a way it makes sense to them. This is a visualisation type that is frequently used in the context of pharmaceutical research projects to visualise search result properties such as the phase and area associated with search results relating to pharmaceutical projects. Such a visualisation could efficiently enable selection and analysis of the effort being spent on a particular phase of a pharmaceutical research project.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A data processing system for adaptive visualisation of faceted search results comprising:
   an input configured to receive a search query;
   a retriever connected to said input and configured to receive from said input said search query, and retrieve a plurality of search results in function of said search query, each of said search results comprising a plurality of search result properties of which at least one of the search result properties is a search result facet;
   a data type determiner connected to said retriever and configured to receive one or more of said search result facets from said retriever and determine the data type of one or more of said search result facets;
   a visualisation type associator connected to said data type determiner and configured to receive said data type from said data type determiner, and associate a visualisation type with said data type in function of a predetermined visualisation correlation between said data type and said visualisation type;
   a visualizer connected to said visualisation type associator and said retriever and configured to receive said one or more search result facets from said retriever and said visualisation types from said visualisation type associator, present said one or more search result facets by a visualisation in function of said visualisation types to one or more users, and present a visualisation modifier user interface to said one or more users configured to request a visualisation type modification by said one or more users of the visualisation type of said presented visualisation;
   a modification aggregator connected to said visualizer and configured to receive said visualisation type modifications from said visualizer, and aggregate said visualisation type modifications;
   a correlation adaptor connected to said modification aggregator and said visualisation type associator, and being configured to exchange said aggregated visualisation type modifications with said modification aggregator and said predetermined visualisation correlation with said visualisation type associator, and adapt said predetermined visualisation correlation between said data types of said search result facets and said visualisation types in function of said aggregated visualisation type modifications.

2. A data processing system according to claim 1, wherein:
   said retriever is further configured to retrieve a plurality of search results of which at least one of the search result properties is a non-facet search result property that is not a search result facet;
   said data type determiner is further configured to determine the data type of said non-facet search result properties;
   said visualizer is further configured to receive said one or more non-facet search result properties from said retriever and said visualisation types from said visualisation type associator, present said one or more non-facet search result properties by a visualisation in function of said visualisation types to one or more users, and present visualisation modifiers to said one or more users configured to request a visualisation type modification by said one or more users of the visualisation type of said presented visualisations.

3. A data processing system according to claim 1, wherein the correlation adaptor is further configured adapt said predetermined visualisation correlation when said aggregated visualisation type modifications exceed a predetermined threshold.

4. A data processing system according to claim 3, wherein:
   a modification aggregator is further configured to aggregate visualisation type non-modifications of said presented visualisation types by said one or more users; and
   the correlation adaptor is further configured to determine said predetermined threshold as a predetermined rate of said aggregated visualisation type modifications versus said aggregated visualisation type non-modifications.

5. A data processing system according to claim 1, wherein said visualisation types comprise one or more of the following:
   a bar chart;
   a pie chart;
   a one dimensional range;
   a two dimensional heat map;
   a hierarchical, multi-dimensional tree
   a Molecule Viewer;
   a Pathway View;
   a Protein Interaction View;
   a Sequence Alignment View.

6. A data processing system according to claim 1, wherein:
   the visualizer is further configured to present a visualisation in function of said visualisation types to one or more users comprising a range selector configured to request a range selection of a range of values associated with said search result facets, and exchange said range selection with said retriever;
   said retriever is further configured to adapt said search query by said range selection, and retrieve a plurality of search results in function of said adapted search query.

7. A computer implemented method for adaptive visualisation of faceted search results comprising the steps of:
   receiving a search query;
   retrieving a plurality of search results in function of said search query, each of said search results comprising a plurality of search result properties of which at least one of the search result properties is a search result facet;
   determining the data type of one or more of said search result facets;
   associating a visualisation type with said data type in function of a predetermined visualisation correlation between said data type and said visualisation type;
   presenting said one or more search result facets by a visualisation in function of said visualisation types to one or more users;
   presenting a visualisation modifier user interface to said one or more users configured to request a visualisation type modification by said one or more users of the visualisation type of said presented visualisation;
   aggregating said visualisation type modifications;
   adapting said predetermined visualisation correlation between said data types of said search result facets and said visualisation types in function of said aggregated visualisation type modifications.

8. A computer implemented method according to claim 7, wherein said method further comprises the steps of:

determining the data type of at least one of the search result properties that is a non-facet search result property which is not a search result facet;

associating a visualisation type with said data type of said one or more non-facet search result properties in function of the predetermined property visualisation correlation between said data types of said non-facet search result properties and said visualisation types;

presenting said one or more non-facet search result properties in function of said visualisation types to one or more users;

presenting visualisation modifiers to said one or more users configured to request a visualisation type modification by said one or more users of the visualisation type of said presented visualisation;

aggregating said visualisation type modifications;

adapting said predetermined visualisation correlation between said data types of said non-facet search result properties and said visualisation types in function of said aggregated visualisation type modifications.

9. A method according to claim 7, wherein it comprises the step of adapting said predetermined facet visualisation correlation when said aggregated visualisation type modifications exceed a predetermined threshold.

10. A method according to claim 7, wherein said visualisation types comprise one or more of the following:
    a bar chart;
    a pie chart;
    a one dimensional range;
    a two dimensional heat map;
    a hierarchical, multi-dimensional tree.

11. A method according to claim 10, wherein it further comprises the step of:
    aggregating visualisation type non-modifications of said presented visualisation types by said one or more users; and
    determining said predetermined threshold as a predetermined rate of said aggregated visualisation type modifications versus said aggregated non-modifications.

12. A method according to claim 7, wherein said method comprises the further steps of:
    presenting a visualisation in function of said visualisation types to one or more user, the visualisation comprising a range selector configured to request a range selection of a range of values associated with said search result facets;
    adapting said search query by said selection;
    retrieving a plurality of search results in function of said adapted search query.

13. A computer readable medium comprising computer-executable instructions, which when executed by a data processing system, cause the data processing system to perform the following:
    receive a search query;
    retrieve a plurality of search results in function of said search query, each of said search results comprising a plurality of search result properties of which at least one of the search result properties is a search result facet;
    determine the data type of one or more of said search result facets;
    associate a visualisation type with said data type in function of a predetermined visualisation correlation between said data type and said visualisation type;
    present said one or more search result facets by a visualisation in function of said visualisation types to one or more users;
    present a visualisation modifier user interface to said one or more users configured to request a visualisation type modification by said one or more users of the visualisation type of said presented visualisation;
    aggregate said visualisation type modifications; and
    adapt said predetermined visualisation correlation between said data types of said search result facets and said visualisation types in function of said aggregated visualisation type modifications.

* * * * *